(12) United States Patent
Nordman

(10) Patent No.: US 6,176,991 B1
(45) Date of Patent: *Jan. 23, 2001

(54) SERPENTINE CHANNEL WITH SELF-CORRECTING BENDS

(75) Inventor: Eric S. Nordman, Palo Alto, CA (US)

(73) Assignee: The Perkin-Elmer Corporation, Foster City, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/191,417

(22) Filed: Nov. 12, 1998

Related U.S. Application Data
(60) Provisional application No. 60/065,100, filed on Nov. 12, 1997.

(51) Int. Cl.[7] ............................................. C02F 1/40
(52) U.S. Cl. ........................ 204/601; 204/450; 204/451; 204/600; 422/102; 435/288.5
(58) Field of Search ....................... 204/450, 451, 204/452, 453, 454, 455, 600, 601, 602, 603, 604, 605; 422/102; 435/288.5

(56) References Cited

U.S. PATENT DOCUMENTS

| | | | |
|---|---|---|---|
| 5,599,432 | 2/1997 | Manz et al. | 204/451 |
| 5,958,694 * | 12/1999 | Nikiforov | 435/6 |
| 5,993,750 * | 11/1999 | Ghosh et al. | 422/191 |
| 6,033,546 * | 3/2000 | Ramsey | 204/603 |
| 6,033,628 * | 3/2000 | Kaltenbach et al. | 422/68.1 |

FOREIGN PATENT DOCUMENTS

| | | |
|---|---|---|
| 91/16966 | 11/1991 | (WO) . |
| 96/04547 | 2/1996 | (WO) . |

OTHER PUBLICATIONS

Jacobson, S.C., et al., "Effects of Injection Schemes and Column Geometry on the Performance of Microchip Electrophoresis Devices" *Anal. Chem.* (1994) 66:1107–1113.

Jacobson, S.C., and Ramsey J.M., "Microchip electrophoresis with sample stacking," Electrophoresis 16:481–486 (1995).

Jacobson, S.C., et al., "Open Channel Electrochromatography on a Microchip," Anal. Chem. 66:2369–2373 (1994).

* cited by examiner

*Primary Examiner*—Jill Warden
*Assistant Examiner*—John S. Starsiak, Jr.
(74) *Attorney, Agent, or Firm*—Peter J. Dehlinger

(57) ABSTRACT

A serpentine electrophoresis channel, e.g., for a microchip format, is disclosed. The channel includes pairs of linear segments, e.g., parallel or right-angle segments, each joined by an angled channel region having a first curved channel portion subtending an angle $\alpha_f > \alpha$, where $\alpha$ is the angle between segments in a pair, and a second curved channel portion subtending an angle $\alpha_s = \alpha_f - \alpha$. The angles and cross-sections of the two channel portions are such that $\delta t_f$, the time differential of analyte migration at inner and outer tracks in the first curved portion is equal to $\delta t_s$, the time differential of analyte migration at outer and inner tracks in the second curved portion, respectively.

30 Claims, 3 Drawing Sheets

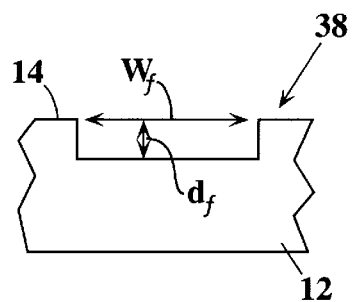
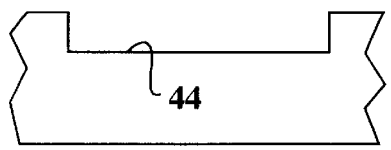
Fig. 3A        Fig. 3B
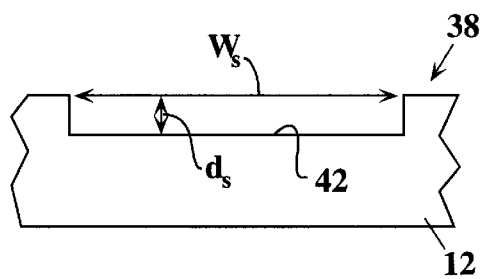
Fig. 3C
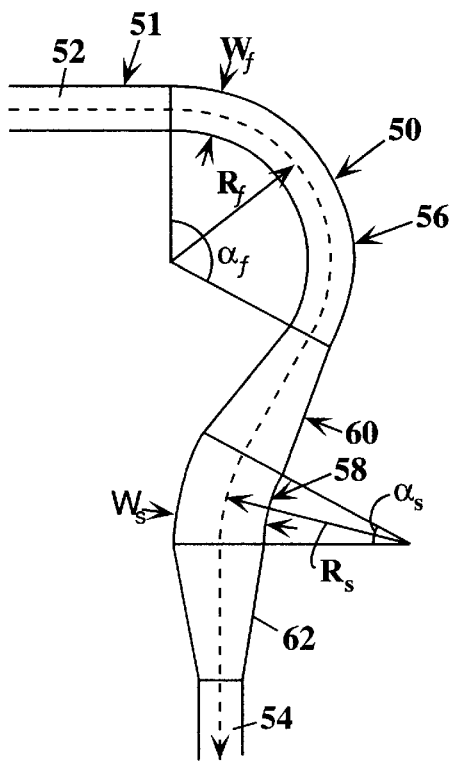
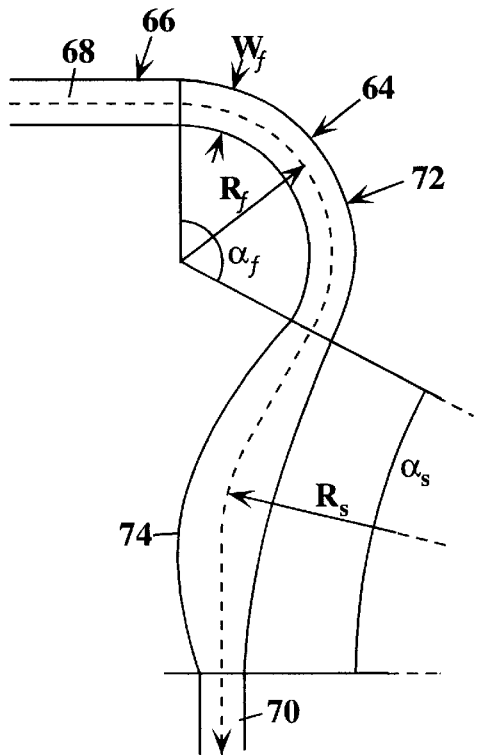
Fig. 4        Fig. 5

US 6,176,991 B1

SERPENTINE CHANNEL WITH SELF-CORRECTING BENDS

This application claims the priority of U.S. Provisional Application Ser. No. 60/065,100 filed Nov. 12, 1997, which is incorporated herein by reference.

FIELD OF THE INVENTION

The present invention relates to electrophoretic separation devices, and in particular, to a device having a serpentine separation channel, for example, in a microfabricated device.

BACKGROUND OF THE INVENTION

Electrophoresis exploits the differential rate of migration of charged species through a separation medium, under the influence of an electric field, for purposes of separating and/or characterizing physical properties of the charged species. Typically, the sample containing the charged species to be separated is placed at one end of a separation channel (which may be a linear channel or a lane in a 2-dimensional slab) and a voltage difference is placed across opposite channel ends until a desired migration end point is reached. The separated analyte molecules may then be detected, e.g., by optical detection, radiography, or band elution.

As examples, gel electrophoresis in the presence of a charged surfactant, such as dodecyl sulfate, is widely used for protein separation and for characterizing protein molecular weight. Electrophoresis in a gel or liquid medium is commonly used to separate oligonucleotides with different numbers of bases, for example, in DNA sequencing.

One of the possible applications of microfabrication techniques that has been proposed is in the area of column separation devices, including electrophoresis devices. Jacobsen, et al. (*Anal. Chem.* 66:2369 (1994); *Electrophoresis* 16:481 (1995) have described a "microchip" electrophoresis device formed by etching an open electrophoresis channel, and suitable connecting reservoirs, on a glass slide. Because of the small chip dimensions, typically less than 10–15 cm on a side, it is necessary to form the separation column in the form of a serpentine pathway in order to achieve total column separation lengths suitable for most applications.

Although a serpentine column solves the problem of adequate column length on a microchip, it introduces a potentially serious limitation in terms of column resolution. When a electrophoretic band is migrating through a linear channel, the molecules making up the band, which are all migrating at roughly the same speed, tend to migrate as a tight band. However, the same molecules migrating through a turn in a serpentine pathway will migrate through the shorter inner side of the channel faster than through the longer outer side of the channel, leading to band spreading and nonuniformity across the width of the channel. At each turn in the pathway, more band resolution is lost. Heretofore, this problem has severely limited the range of practical electrophoresis applications in a microchip format.

SUMMARY OF THE INVENTION

The application includes, in one aspect, an electrophoresis channel through which one or more charged species are intended to migrate under the influence of a voltage difference placed across opposite ends of the channel. The channel includes (i) a pair of channel segments disposed at an angle a with respect to one another, and (ii) an angled channel region connecting the two channel segments.

The angled channel region has a first curved channel portion subtending an angle $\alpha_f > \alpha$, where $\alpha$ is the angle between the two channel segments, and a second curved channel portion subtending an angle $\alpha_s = \alpha_f - \alpha$. The first curved portion defines inner and outer tracks or channel sides, such that an analyte migrating through the first channel portion under the influence of such voltage difference will traverse the inner track in a time interval $\delta t_f$ faster than that of the same analyte traversing the outer track. The second curved portion defines second inner and outer tracks such that an analyte migrating through the second channel portion under the influence of the same voltage difference will traverse the outer track in a time interval $\delta t_s$ faster than that of the same analyte traversing the inner track. The angles and cross-sections of the two channel portions are such that $\delta t_f$ is approximately equal to $\delta t_s$.

The channel is typically part of a serpentine pathway containing a plurality of such segments, each pair of adjacent channel segments being connected by an associated angled channel region.

Where the two channel segments are disposed at right angles with respect to one another, $\alpha_f$ is preferably between about 110° and 160°, and $\alpha_s$, between about 20° and 70°, respectively. Where the two channel segments are disposed substantially parallel to one another, $\alpha_f$ is preferably between about 200° and 250°, and $\alpha_s$, between about 20° and 70°, respectively.

In a microfabricated chip format, the channel has preferred width dimensions between about 25–250 microns, and preferred depth dimensions between about 5–100 microns.

In one general embodiment, the first and second curved portions have substantially constant channel widths $W_f$ and $W_s$, respectively, where $W_f < W_s$. In this embodiment, the angled channel region further includes tapered-width segments joining the second curved channel portion to the first channel portion and to one of the two channel segments. An approximate relationship between $W_f$ and $W_s$ is given by the relationship $W_s = (\alpha_f W_f^2 R_f / \alpha_s R_s)^{1/2}$, where $R_f$ and $R_s$ are the radii of curvature of the first and second curved portions, respectively.

In another general embodiment, the first curved channel portion has a preferably fixed channel width, and the second channel portion, a variable width that expands on progressing inwardly from each end.

In yet another embodiment, the first curved channel portion has a channel depth which increases on progressing toward the second channel portion, and the second curved channel portion has a channel depth which decreases on progressing away from the first curved channel portion. The channel width may be substantially constant in the channel segments and the channel connecting region therebetween.

More generally, the invention includes an analyte separation channel through which one or more analytes is intended to migrate under the influence of a motive force applied to opposite ends of the channel. The device includes (i) a pair of channel segments disposed at an angle $\alpha$ with respect to one another, and (ii) an angled channel region of the type just described connecting the two channel segments. The motive force may be a voltage difference applied across the opposite ends of the channel, or a force producing fluid movement through the channel or a combination of the two.

In a related aspect, the invention includes a microfabricated device for electrophoretic separation of analytes in a mixture. The device includes a substantially planar-surface substrate having formed thereon, first and second reservoirs and a serpentine electrophoretic channel extending therebetween. The channel has a plurality of linear segments, and connecting the adjacent ends of each pair of adjacent segments, an angled channel region of the type described above. The channel, including the linear segments and angled channel regions, has preferred channel width dimensions between about 25–250 microns, and depth dimensions between about 5–100 microns.

These and other objects and features of the invention will become more fully apparent when the following detailed description of the invention is read in conjunction with the accompanying drawings.

BRIEF DESCRIPTION OF THE DRAWINGS

FIGS. 3A–3C are sectional views taken along lines 3A–3A, 3B–3B, and 3C–3C, respectively, in FIG. 2;

FIG. 4 is an enlarged view of a 90° bend in a serpentine channel formed in accordance with one embodiment of the present invention;

FIG. 5 is an enlarged view of a 90° bend in a serpentine channel formed in accordance with another embodiment of the invention;

DETAILED DESCRIPTION OF THE INVENTION

Figure 1:
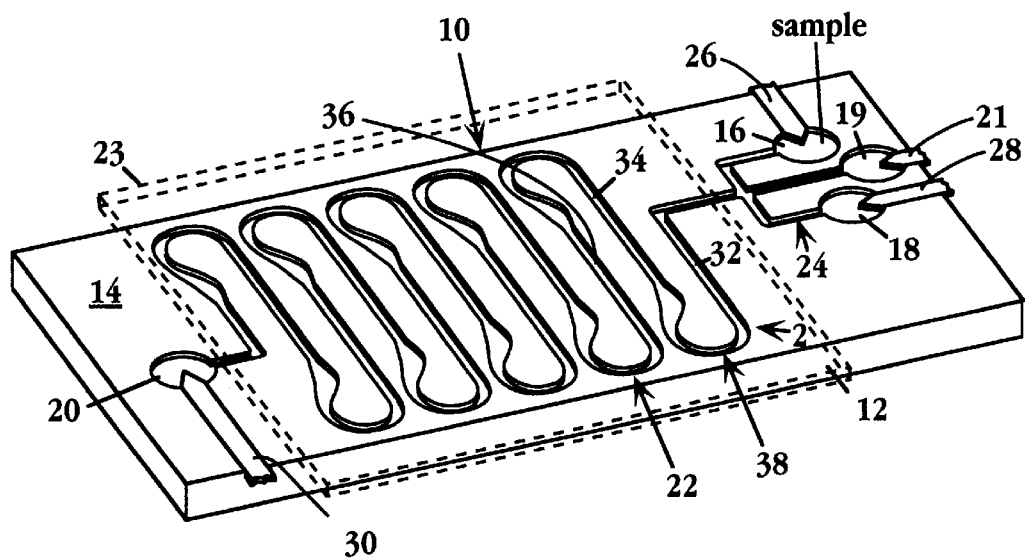
FIG. 1 is a perspective view of a microfabricated device constructed according to the present invention, having an open electrophoresis channel and liquid reservoirs formed on a substrate.

FIG. 1 shows a microfabricated device 10 constructed in accordance with the invention, for electrophoretic separation and/or characterization of one or more analytes in a sample mixture. The device generally includes a planar substrate 12 having formed in its upper surface 14, open reservoirs 16, 18, 19, and 20, and a serpentine electrophoresis channel 22 connecting the reservoirs. Reservoirs 18 and 16, which are intended to contain electrophoresis buffer and sample fluid, respectively, are connected in fluid communication with each other and with channel 22 through a fork-like connector 24. Reservoirs 19, 20 are intended to hold the waste reservoir. The four reservoirs are connected to electrodes 26, 28, 21, and 30, as shown, which are in turn connected to suitable voltage leads during operation of the device, for (i) loading sample from reservoir 16 into channel 22, by applying a voltage across electrodes 26, 28, and (ii) (ii) electrophoretically separating charged sample components, by applying a voltage difference across opposite ends of the channel, i.e., across electrodes 21, 30.

With continued reference to FIG. 1, channel 22 includes a plurality of parallel linear channel segments, such as segments 32, 34, and 36, and curved channel regions connecting the adjacent ends of adjacent linear segments, such as curved channel region 38 connecting adjacent ends of segments 32, 34. In a typical embodiment, the substrate or chip has side dimensions of between about 1 to 15 cm, and the linear segments are each about 0.5 to 10 cm in length. Thus, for example, a channel having 30 linear segments, each about 8 mm in length has a column length, ignoring the lengths of the connecting regions, of about 250 mm. With the added lengths of the connecting regions, the total length may be in the 30 cm range, on a chip whose side dimensions may be as little as 1 cm. A coverslip 23 placed over the portion of the substrate having the serpentine channel serves to enclose the channel, although an open serpentine channel is also contemplated.

Figure 2:
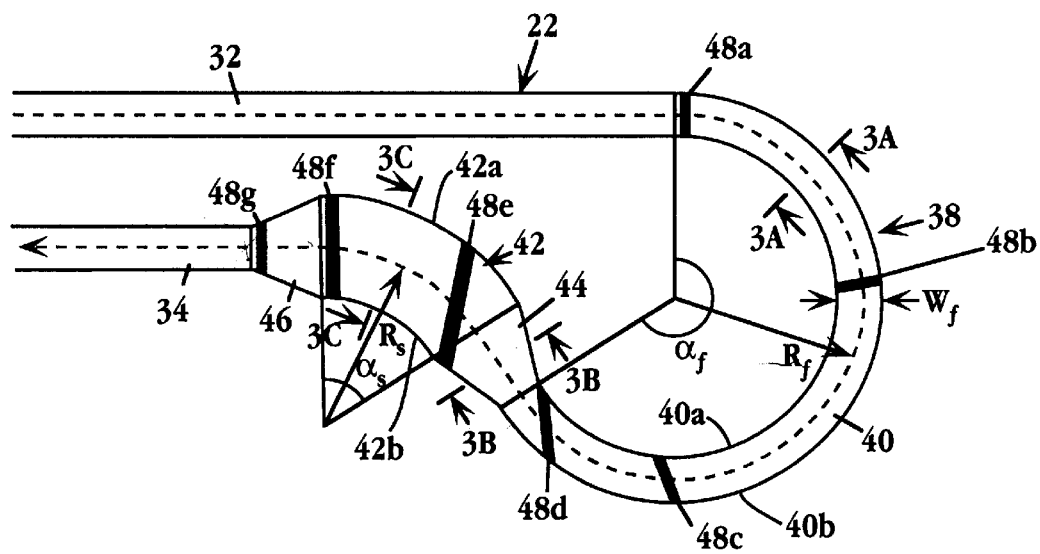
FIG. 2 is an enlarged view of a 180° bend in a serpentine channel formed in accordance with the present invention, illustrating the effect of the self-correcting bend on band distortion.

The construction of a curved connecting region—in this case, region 38—is shown in enlarged plan view in FIG. 2, which shows portions of linear segments 32, 34 connected by the region. The region includes a first curved channel portion 40 which subtends an angle $\alpha_f$ which is greater than the minimum angle $\alpha$ needed to connect the two segments. Where, as here, the linear segments are parallel and $\alpha$ is 180°, $\alpha_f$ is typically between about 200°–250°, i.e., about 20°–70° over the minimum angle. As shown, portion 40 has a substantially constant channel width $W_f$ along its length, equal to the channel width of the connected linear segments.

As seen in FIG. 3A, which is a cross-section along line 3A–3A in FIG. 2, the channel has a substantially rectangular cross-section with a width dimension $W_f$ and depth dimension $d_f$. $W_f$ is typically between about 25–200, preferably 50–100 microns, and $d_f$ is typically about 5–100, preferably 25–75 microns.

With continued reference to FIG. 2. portion 38 includes a second curved channel portion 42 subtending an angle $\alpha_s$ which corrects the overangle $\alpha_f$ to provide the desired 180° total angle in the curved portion; that is, $\alpha_s = \alpha_f - \alpha$. Thus, for example, where $\alpha$ is 180°, and $\alpha_f$ is between about 210° and 250°, $\alpha_s$ is between about 20° and 70°, respectively. The width $W_s$ of the second curved portion is greater than $W_f$ and is selected, in relation to the two angles $\alpha_f$ and $\alpha_s$, and in accordance with the invention, to correct band distortion produced as a band moves through portion 40, as will be described below. In the embodiment illustrated, and as shown in FIG. 3C, $W_s$ is greater than $W_f$, acting in effect reduce the electric field strength on analyte molecules migrating through this portion, relative to portion 40. As seen in FIG. 3C, the channel depth $d_s$ in portion 42 is the same as that in portion 40, i.e., $d_s = d_f$.

Channel region 38 further includes two tapered-width segments 44, 46, which serve as interfaces between (i) the smaller-width portion 40 and the larger-width portion 42 (segment 44) and between (ii) the larger-width portion 42 and the smaller-width linear segment 34(segment 46). A cross-sectional view of segment 44 is shown in FIG. 3B, showing a channel width intermediate between that of portions 40, 42, and the same channel depth.

The operation of the second channel portion, in correcting curved channel effects produced in the first channel portion, will now be discussed, also with reference to FIG. 2. In this figure, a charged species migrating as a band through the channel is indicated at various stages through the curved channel regions by numerals 48a–48g. Band 48a, which is at the position just entering the curved channel portion, is substantially undistorted, meaning that the band is both narrow and disposed along an axis substantially normal to the channel axis. As the band enters channel portion 40, it begins to distort, as shown at 48b, due to the shorter migration distance of molecules along the inner track 40a and the longer migration distance of molecules along the outer track 40b. The distortion increases progressively as the band migrates through portion 40, as illustrated by bands 48c and 48d.

It can be shown that a band on the inside track will lead a band on the outside track with a time $\delta t_f$ approximately equal to $\alpha_f(2W_fR_f)/\mu E_{f\text{-}center}$, where $R_f$ is the radius of curvature of curved portion 40, $W_f$ is the channel width, $\mu$ is the mobility of the migrating species, in m²/Vsec, and $E_{f\text{-}center}$ is the electric field in portion 40 at the center of the track, resulting from the potential difference applied across opposite ends of the channel.

The purpose of the second curved portion is to provide a correction, on the opposite channel side, for the band distortion produced in the first curved portion. Briefly, this second curved portion is designed such that a band on the inside track 42b (which is the shorter of the two tracks) will lead the band on the outside track 42a by a time $\delta t_s$ substantially equal to $\delta t_f$. Similar to the calculation above, it can be shown that $\delta t_s$ is approximately equal to $\alpha_s(2W_sR_s)/\mu E_{s\text{-}center}$, where $R_s$ is the radius of curvature of curved portion 42, $W_s$ is the channel width, $\mu$ is the mobility of the migrating species, in m²/Vsec, and $E_{s\text{-}center}$ is the electric field in portion 42 at the center of the track, also due to the same potential difference applied across the ends of the channel. It is noted that $E_{s\text{-}center}$ is less than $E_{f\text{-}center}$, due to the larger channel width in channel 42, according to the relationship $E_s = E_f(W_f/W_s)$. The condition $\delta t_f = \delta t_s$ is satisfied when $\alpha_f(2W_fR_f)/\mu E_{f\text{-}center} = \alpha_s(2W_sR_s)/\mu E_{s\text{-}center}$, that is, when $\alpha_f/\alpha_s = W_s^2 R_s / W_f^2 R_f$. As an example, assume $W_f$ is 50 $\mu$m, $\alpha_s$ is 210° $\alpha_s$ is 30°, and $R_f = R_s = 1$ mm. $W_s$ is then $((50 \mu m)^2(210/30))^{1/2}$, or about 132 $\mu$m.

With reference again to FIG. 2, it can be appreciated that band 48d migrates through tapered segment 44 substantially without correction, is fully corrected within portion 42, and then migrates through segment 46 and into segment 34 in corrected form, i.e., with the band axis oriented substantially normal to the segment axis.

FIG. 4 shows an embodiment of a 90° curved channel region 50 constructed in accordance with the invention, for use, for example, in a serpentine channel of the type described above, but where each 180° turn is produced by two adjoining 90° turns. Channel region 50 joins two linear channel segments 52, 54 which in this embodiment are disposed at right angles with respect to one another.

Channel region 50 includes a first curved channel portion 56 which subtends an angle $\alpha_f$ which is greater than 90°, and a second channel portion 58 which subtends an angle $\alpha_s$ which corrects the overangle $\alpha_f$ to provide the desired 90° total angle in the curved portion; that is, $\alpha_s = \alpha_f - \alpha$. In the $\alpha = 90$ embodiment, $\alpha_f$ is typically between about 110° and 160°, and $\alpha_s$ is between about 20° and 70°, respectively. As in the 180° embodiment, the width $W_s$ of the second curved portion is greater than $W_f$ and is selected, in relation to the two angles $\alpha_f$ and $\alpha_s$, and in accordance with the invention, to correct band distortion produced as a band moves through portion 56, as will be described below. In the embodiment illustrated, where the channel depth is uniform throughout the channel region $W_s$ is greater than $W_f$, and related through the relationship $\alpha_f(2W_fR_f)/\mu E_{s\text{-}center} = \alpha_s(2W_sR_s)/\mu E_{f\text{-}center}$, or equivalently, when $\alpha_f/\alpha_s = W_s^2 R_s / W_f^2 R_f$, where $R_f$, $R_s$, $\mu$, $E_{f\text{-}center}$, and $E_{f\text{-}center}$ are as above. As an example, assume $W_f$ is 50 $\mu$m, $\alpha_f$ is 120° and $\alpha_s$ is 30°, and $R_f = R_s = 1$ mm. $W_s$ is then $(50 \mu m^2(120/30))^{1/2}$, or 100 $\mu$m.

Region 50 further includes tapered segments 60, 62 which serve as interfaces between (i) the smaller-width portion 56 and the larger-width portion 58, and (ii) the larger-width portion 58 and the smaller-width linear segment 54.

Analogous to the band behavior in the 180° turn region 38, an analyte band migrating into portion 56, substantially normal to the axis of segment 52, will become distorted by its migration through portion 56, with the outer-side of the band trailing the inner side of the band. The analyte migrates through tapered segment 60 substantially without correction, is fully corrected within portion 58 and then migrates through segment 62 and into segment 54 in corrected form, i.e., with the band axis oriented substantially normal to the segment axis.

FIG. 5 shows another embodiment of a 90° curved channel region 64 constructed in accordance with the invention, for use, for example, in a serpentine channel 66 of the type described above. Channel region 64 joins two linear channel segments 68, 70 which in this embodiment are disposed at right angles with respect to one another. Channel region 64 includes a first curved channel portion 72 subtending an angle $\alpha_f$ which is greater than 90°, and a second channel portion 74 subtending an angle $\alpha_s$ which corrects the overangle $\alpha_f$ to provided the desired 90° total angle in the curved portion.

This embodiment differs from the one illustrated in FIG. 4 in that curved portion 74 replaces portion 58 and the two tapered segments 60, 62 in portion 58, as a continuously curved portion. That is, $W_s$ is continuously variable through portion 74, from a minimum width $W_s$ to a maximum width $W_{s\text{-}max}$. Exemplary angles $\alpha_s$, $\alpha_f$, are as above, where the radius of curvature $R_s$ of portion 74 is about 3–4 times that in the FIG. 4 embodiment, but the angle $\alpha_s$ subtending the portion is about the same in both embodiments. The relationship between $W_s$ and $W_f$ is more complex than that shown above, but can be determined from the relationships given above, by integrating over $\alpha_s$, where the value of $W_s$ varies continuously over portion 74 according to a known angle-dependent relationship.

The operation of portion 74 in correcting band distortion produced in portion 72 is substantially as described above, but where band correction occurs over the entire region between portion 72 and segment 70.

Figure 6:
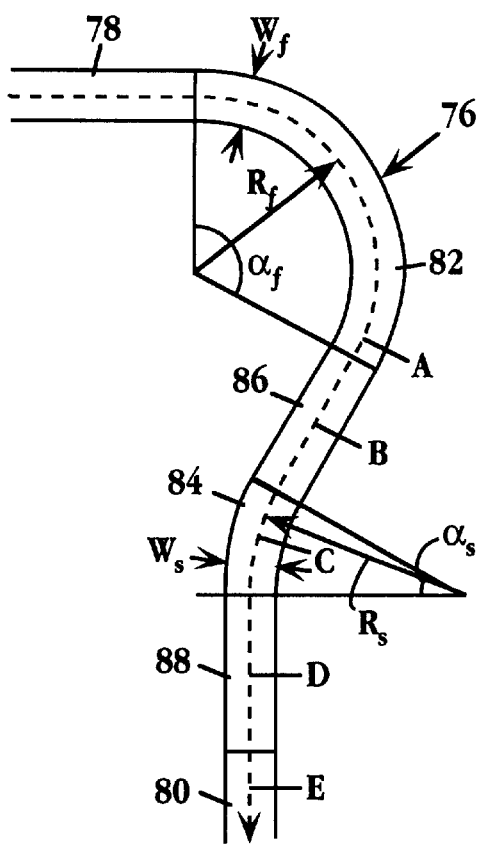
FIG. 6 is an enlarged view of a 90° bend in a serpentine channel formed in accordance with yet another embodiment of the invention.

Still another embodiment of the invention, for a 90° turn, is illustrated by angle channel region 76 in FIG. 6. The channel region, which joins right-angle channel segments 78, 80, includes a first curved channel portion 82 subtending an angle $\alpha_f > 90°$, and a second curved channel portion 84 subtending an angle $\alpha_s$, which corrects the overangle $\alpha_f$ to provide the desired 90° total angle in the curved portion. Also forming part of the channel region are interface segments 86, 88 connecting portion 82 to portion 84, and portion 84 to segment 80, respectively. Exemplary $\alpha_f$ and $\alpha_s$ are as above.

Figure 7:
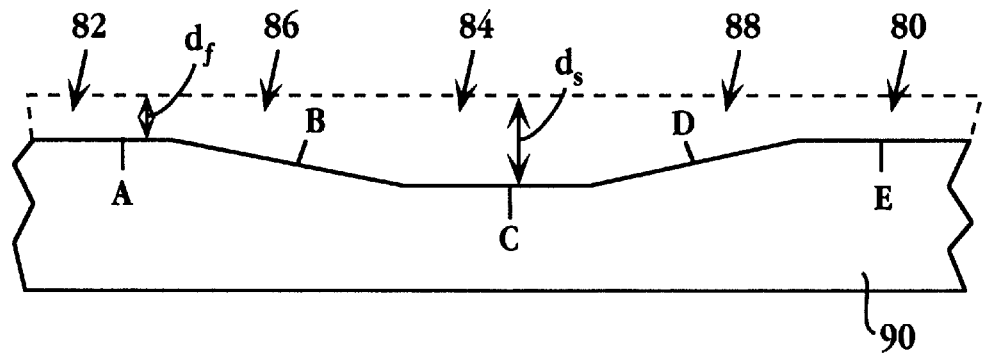
FIG. 7 is a cross-section of the channel region in FIG. 6, taken along the channel pathway 7—7 in FIG. 6.

The embodiment differs from those above in that the width $W_f$ of portion 84 is the same the width $W_s$ of portion 82, but portion 84 has a depth $d_s$ which is greater than $d_f$, as illustrated in FIG. 7, which shows a segmented cross-section (through segments indicated by A, B, C, D, and E) along indicated portions of region 76. Also as seen, interface segments 86, 88 have tapered channel depths, rather than the tapered channel widths of the interface segments in the earlier described embodiments.

The electric field $E_s$ in portion 84 is equal to $E_f(d_f/d_s)$, and band correction ($\delta t_f = \delta t_s$) occurs when $\alpha_f(2W_fR_f)/\mu E_{f\text{-}center} = \alpha_s(2W_sR_s)/\mu E_{s\text{-}center}$, that is, when $\alpha_f/\alpha_s = W_s d_s R_s / W_f d_f R_f = d_s R_s / d_f R_f$. As an example, assume that $W_s = W_f$, $d_f$ is 50 $\mu$m, $\alpha_f$ is 120° and $\alpha_f$ is 30°, and $R_f = R_s = 1$ mm. $d_s$ is then $(50 \mu m)(120/30)$, or about 200 $\mu$m.

The operation of region 76 in correcting band distortion is similar to that described above, for example, with respect to the embodiment shown in FIG. 4. Briefly, a band becomes distorted by its migration through portion 82, with the outer-side of the band trailing the inner side of the band. The band migrates through tapered segment 86 substantially without correction, is fully corrected within portion 84 and then migrates through segment 88 and into segment 80 in corrected form, i.e., with the band axis oriented substantially normal to the segment axis.

From the foregoing, it can be appreciated how various objects and features of the invention are met. The invention is compatible with tightly coiled serpentine electrophoresis or other chromatographic channel configurations formed in a small-area microchip, for example, using conventional microfabrication techniques. The microfabrication method may involve either same-depth, variable-width etching, or same-width, variable depth etching, or a combination of the two.

The self-correcting bend feature of the invention acts to correct distortion produced by band migration around a turn, due to slower migration at the outside of the turn, acting to preserve band resolution along the entire channel length, which may include numerous turns, typically 90° or 180° turns.

Although the invention has been described with respect to specific embodiments, it will be appreciated that a variety of modifications may be made within the scope of the claimed invention. For example, the serpentine channel may be formed by chemical or laser etching techniques on a relatively large-scale plate, e.g., a 10 cm×10 cm plate designed for preparative electrophoresis or chromatography. The serpentine channel may be formed in a closed tube, such as a capillary electrophoresis tube, where each turn in the tube includes an expanded diameter, self-correcting counter turn. In still another aspect, the self-correcting turn may apply to other types of chromatography channels or tubes, dependent on pressurized fluid flow or gravity rather than a voltage difference as a motive force for moving analyte molecules through a separation medium.

It is claimed:

1. An electrophoresis channel through which one or more analytes are intended to migrate under the influence of a voltage difference applied across opposite ends of the channel, comprising
    (i) a pair of channel segments disposed at an angle $\alpha$ with respect to one another, and
    (ii) an angled channel region connecting the two channel segments, said region having
    (a) a first curved channel portion subtending an angle $\alpha_f > \alpha$, and defining first inner and outer tracks such that an analyte migrating through the first channel portion under the influence of such voltage difference will traverse the inner track in a time interval $\delta t_f$ faster than that of the same analyte traversing the outer track, and
    (b) a second curved channel portion subtending an angle $\alpha_s = \alpha_f - \alpha$, and defining second inner and outer tracks such that an analyte migrating through the second channel portion under the influence of the same voltage difference will traverse the outer track in a time interval $\delta t_s$ faster than that of the same analyte traversing the inner track,
    where the cross-sections of said curved channel portions are such that $\delta t_f$ is approximately equal to $\delta t_s$.

2. The channel of claim 1, wherein the two channel segments are disposed at right angles with respect to one another, $\alpha_f$ is between about 110° and 160°, and $\alpha_s$ is between about 20° and 70°, respectively.

3. The channel of claim 1, wherein the two channel segments are disposed substantially parallel to one another, $\alpha_f$ is between about 200° and 250°, and $\alpha_s$ is between about 20° and 70°, respectively.

4. The channel of claim 1, which is formed in a microfabricated chip, and has channel width dimensions between about 25–250 microns, and depth dimensions between about 5 and 100 microns.

5. The analyte separation channel of claim 1, which is part of a serpentine pathway containing a plurality of such pairs of channel segments.

6. The channel of claim 1, wherein the first and second curved portions have substantially constant channel widths $W_f$ and $W_s$, respectively, where $W_f < W_s$, and the angled channel region further includes tapered-width segments joining the second curved channel portion to the first channel portion and to one of the two channel segments.

7. The channel of claim 6, wherein $W_s = (\alpha_f W_f^2 R_f / \alpha_s R_s)^{1/2}$, where $R_f$ and $R_s$ are the radii of curvature of the first and second curved portions, respectively.

8. The channel of claim 1, wherein the first curved channel portion has a fixed channel width, and the second channel portion has a variable width that expands on progressing inwardly from each end.

9. The channel of claim 1, wherein the first curved channel portion has a channel depth which increases on progressing toward the second channel portion, and the second curved channel portion has a channel depth which decreases on progressing away from the first curved channel portion.

10. The channel of claim 9, whose channel width is substantially constant in the channel segments and the channel connecting region therebetween.

11. An analyte separation channel through which one or more analytes is intended to migrate under the influence of a motive force applied to opposite ends of the channel, comprising
    (i) a pair of channel segments disposed at an angle $\alpha$ with respect to one another, and
    (ii) an angled channel region connecting the two channel segments, said region having
    (a) a first curved channel portion subtending an angle $\alpha_f > \alpha$, and defining first inner and outer tracks such that an analyte migrating through the first channel portion under the influence of such force will traverse the inner track in a time interval $\delta t_f$ faster than that of the same analyte traversing the outer track, and
    (b) a second curved channel portion subtending an angle $\alpha_s = \alpha_f - \alpha$, and defining second inner and outer tracks such that an analyte migrating through the second channel portion under the influence of the same force will traverse the outer track in a time interval $\delta t_s$ faster than that of the same analyte traversing the inner track,
    where the cross-sections of said curved channel portions are such that $\delta t_f$ is approximately equal to $\delta t_s$.

12. A microfabricated device for electrophoretic separation of analytes in a mixture, comprising
    a substantially planar-surface substrate having formed thereon, first and second reservoirs and a serpentine electrophoretic channel extending therebetween, said channel having:
    a plurality of linear segments, and
    connecting the adjacent ends of each pair of adjacent segments, an angled channel region, each of said regions having
    (a) a first curved channel portion subtending an angle $\alpha_f > \alpha$, where $\alpha$ is the angle between the two channel segments connected by the curved channel portion, and said channel portion defines first inner and outer tracks such that an analyte migrating through the first channel portion under the influence of a voltage difference placed across the two reservoirs will traverse the inner track in a time interval $\delta t_f$ faster than that of the same analyte traversing the outer track, and (b) a second curved channel portion subtending an angle $\alpha_s = \alpha_f - \alpha$, and defining second inner and outer tracks such that an analyte migrating through the second channel portion under the influence of the same voltage difference will traverse the outer track in a time interval $\delta t_s$ faster than that of the same analyte traversing the inner track, where the cross-sections of said curved channel portions are such that $\delta t_f$ is approximately equal to $\delta t_s$.

13. The device of claim 12, wherein the channel segments are disposed substantially parallel to one another, $\alpha_f$ is between about 200° and 250°, and $\alpha_s$ is between about 20° and 70°, respectively.

14. The device of claim 12 which is formed in a microfabricated chip, and has channel width dimensions between about 25–250 microns, and depth dimensions between about 5–100 microns.

15. The device of claim 12, wherein the first and second curved portions have substantially constant channel widths $W_f$ and $W_s$, respectively, where $W_f < W_s$, and the angled channel region further includes tapered-width segments joining the second curved channel portion to the first channel portion and to one of the two associated channel segments.

16. The device of claim 15, wherein $W_s = (\alpha_f W_f^2 R_f / \alpha_s R_s)^{1/2}$, where $R_f$ and $R_s$ are the radii of curvature of the first and second curved portions, respectively.

17. The device of claim 12, wherein the first curved channel portion has a fixed channel width, and the second channel portion, a variable width that expands on progressing inwardly from each end.

18. The device of claim 12, wherein the first curved channel portion has a channel depth which increases on progressing toward the second channel portion, and the second curved channel portion has a channel depth which decreases on progressing away from the first curved channel portion.

19. The device of claim 18, whose channel width is substantially constant in the channel segments and the channel connecting regions therebetween.

20. The analyte separation channel of claim 11, wherein the two channel segments are disposed at right angles with respect to one another, $\alpha_f$ is between about 110° and 160°, and $\alpha_s$ is between about 20° and 70°, respectively.

21. The analyte separation channel of claim 11, wherein the two channel segments are disposed substantially parallel to one another, $\alpha_f$ is between about 200° and 250°, and $\alpha_s$ is between about 20° and 70°, respectively.

22. The analyte separation channel of claim 11, which is formed in a microfabricated chip, and has channel width dimensions between about 25–250 microns, and depth dimensions between about 5 and 100 microns.

23. The analyte separation channel of claim 22, which is part of a serpentine pathway containing a plurality of such pairs of channel segments.

24. The analyte separation channel of claim 11, wherein the first and second curved portions have substantially constant channel widths $W_f$ and $W_s$, respectively, where $W_f < W_s$, and the angled channel region further includes tapered-width segments joining the second curved channel portion to the first channel portion and to one of the two channel segments.

25. The analyte separation channel of claim 24, wherein $W_s = (\alpha_f W_f^2 R_f / \alpha_s R_s)^{1/2}$, where $R_f$ and $R_s$ are the radii of curvature of the first and second curved portions, respectively.

26. The analyte separation channel of claim 11, wherein the first curved channel portion has a fixed channel width, and the second channel portion has a variable width that expands on progressing inwardly from each end.

27. The analyte separation channel of claim 11, wherein the first curved channel portion has a channel depth which increases on progressing toward the second channel portion, and the second curved channel portion has a channel depth which decreases on progressing away from the first curved channel portion.

28. The channel of claim 27, whose channel width is substantially constant in the channel segments and the channel connecting region therebetween.

29. The analyte separation channel of claim 12, wherein the two channel segments are disposed at right angles with respect to one another, $\alpha_f$ is between about 110° and 160°, and $\alpha_s$ is between about 20° and 70°, respectively.

30. The analyte separation channel of claim 12, which is part of a serpentine pathway containing a plurality of such pairs of channel segments.

* * * * *

UNITED STATES PATENT AND TRADEMARK OFFICE
CERTIFICATE OF CORRECTION

PATENT NO. : 6,276,991 B1
DATED : August 21, 2001
INVENTOR(S) : Hideaki Kobayashi et al.

It is certified that error appears in the above-identified patent and that said Letters Patent is hereby corrected as shown below:

Column 30,
Lines 39-41, delete "relative to the processing surface, thereby forming the crown on the floating surface of the floating type magnetic head." and substitute -- longitudinal direction thereof. -- in its place.

Column 31,
Line 17, delete "boding" and substitute -- bonding -- in its place.

Signed and Sealed this

Thirtieth Day of April, 2002

Attest:

Attesting Officer

JAMES E. ROGAN
Director of the United States Patent and Trademark Office